United States Patent [19]

Girard et al.

[11] Patent Number: 5,132,319
[45] Date of Patent: Jul. 21, 1992

[54] 1-(HYDROXYLAMINOALKYL) INDOLE DERIVATIVES AS INHIBITORS OF LEUKOTRIENE BIOSYNTHESIS

[75] Inventors: Yves Girard, Lle Bizard; Pierre Hamel, Laval; Daniel Delorme, St. Lazare; Réjean Fortin, Montreal Nord, all of Canada

[73] Assignee: Merck Frosst Canada, Inc., Kirkland, Canada

[21] Appl. No.: 676,631

[22] Filed: Mar. 28, 1991

[51] Int. Cl.$^5$ .................. C07D 209/08; A61K 31/405
[52] U.S. Cl. ..................................... 514/415; 514/418; 548/483; 548/484; 548/485; 548/486; 548/492; 548/495; 548/494; 548/495; 548/510
[58] Field of Search ............... 548/483, 484, 485, 486, 548/492, 493, 510, 494, 495; 514/415, 418

[56] References Cited

U.S. PATENT DOCUMENTS 4,822,809  4/1989  Summers et al. .................... 514/367
4,822,811  4/1989  Summers ............................. 514/411

FOREIGN PATENT DOCUMENTS 279263   8/1988  European Pat. Off. .
292699  11/1988  European Pat. Off. .
89/04299  5/1989  World Int. Prop. O. .

Primary Examiner—Mukund J. Shah
Assistant Examiner—Jyothsna Venkat
Attorney, Agent, or Firm—Gabriel Lopez; Joseph F. DiPrima

[57] ABSTRACT

Compounds having the formula I:

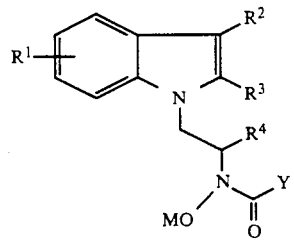

are inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis and allograft rejection and in preventing the formation of atherosclerotic plaques.

8 Claims, No Drawings

1-(HYDROXYLAMINOALKYL) INDOLE DERIVATIVES AS INHIBITORS OF LEUKOTRIENE BIOSYNTHESIS

BACKGROUND OF THE INVENTION

The leukotrienes constitute a group of locally acting hormones, produced in living systems from arachidonic acid. The major leukotrienes are Leukotriene $B_4$ (abbreviated as $LTB_4$), $LTC_4$, $LTD_4$ and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

Structures A, B and C are representative of benzoheterocyclic hydroxylamine derivatives which are described in the prior art, and which have activity as inhibitors of the 5-lipoxygenase enzyme, which results in inhibition of the synthesis of the leukotrienes. The compounds of the present invention, 1-(hydroxylaminoalkyl)indole derivatives are novel in that hydroxylaminoalkyl groups attached to the nitrogen of indole, are unknown in the prior art, representative of which are the following:

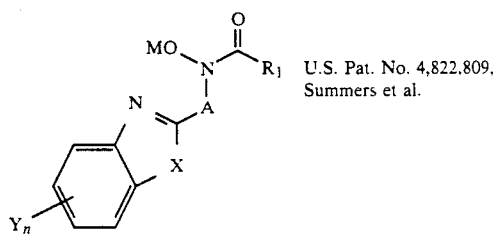

A. U.S. Pat. No. 4,822,809, Summers et al.

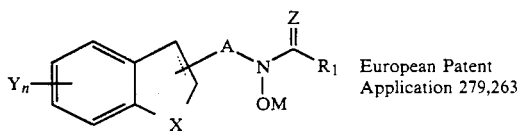

B. European Patent Application 279,263

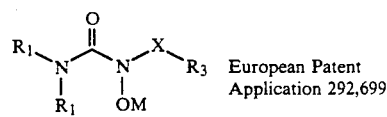

C. European Patent Application 292,699

SUMMARY OF THE INVENTION

The present invention relates to certain 1-(hydroxylaminoalkyl)indoles having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis and allograft rejection and in preventing the formation of atherosclerotic plaques.

DETAILED DESCRIPTION OF THE INVENTION

The present invention provides novel compounds of the formula I:

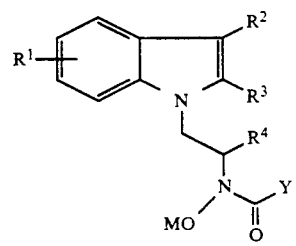

wherein:

$R^1$, $R^2$ and $R^3$ are independently:
a) hydrogen;
b) lower alkyl;
c) cycloalkyl;
d) $CH_2$(phenyl-$R^8$);
e) CN;
f) $NO_2$;
g) $CF_3$;
h) $N_3$;
i) $N(R^5)_2$, $NR^4COR^6$, or $NR^4CON(R^5)_2$;
j) $OR^4$;
k) $SR^7$, $S(O)R^7$, $S(O)_2R^7$, or $S(O)_2; N(R^5)_2$;
l) $COR^6$, $CON(R^5)_2$, $CO_2R^4$; or
m) halogen;

$R^4$ is H or lower alkyl;
$R^5$ is H or loweralkyl, or two $R^5$ groups attached to the same nitrogen may form a saturated ring of 5 or 6 members optionally containing a second heteroatom chosen from O, S, or $NR^4$;
$R^6$ is H, loweralkyl, -phenyl-$R^8$, or $CF_3$;
$R^7$ is lower alkyl, phenyl-$R^8$, or $CF_3$;
$R^8$ is:
a) H;
b) lower alkyl;
c) lower alkylthio;
d) CN;
e) $CF_3$;
f) $N_3$;
g) $NR^4COR^4$;
h) $OR^4$;
i) $COR^4$, $CON(R^5)_2$, or $CO_2R^4$; or
j) halogen;
Y is H, lower alkyl, or $N(R^5)_2$;
M is H, CO(phenyl-$R^8$), or CO-alkyl;
or the pharmaceutical acceptable salts thereof.

DEFINITIONS

The following abbreviations have the indicated meanings:

Ac=acetyl
DMF=dimethylformamide
Et=ethyl
Me=methyl
Ph=phenyl
THF=tetrahydrofuran
r.t.=room temperature
DIBAL=diisobutyl aluminum hydride Alkyl means linear and branched structures and combinations thereof.

"Alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

"Lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, and the like.

"Cycloalkyl" refers to a hydrocarbon containing one or more rings having from 3 to 12 carbon atoms, with the hydrocarbon having up to a total of 20 carbon atoms. Examples of cycloalkyl groups are cyclopropyl, cyclopentyl, cycloheptyl, adamantyl, cyclododecylmethyl, 2-ethyl-1-bicyclo [4.4.0]decyl and the like.

"Lower alkylthio" means alkylthio groups of from 1 to 7 carbon atoms of a straight, branched, or cyclic configuration. Examples of lower alkylthio groups include methylthio ($CH_3S-$), isopropylthio (($CH_3)_2CHS-$) and the like.

Halogen means F, Cl, Br, and I.

It is intended that the definitions of any substituent (e.g., $R^5$, $R^6$, etc.) in a particular molecule be independent of its definitions elsewhere in the molecule. Thus, $-N(R^5)_2$ represents $-NHH$, $-NHCH_3$, $-N(CH_2)_2S$, etc.

The heterocycles formed when two $R^5$ groups join through N include pyrrolidine, piperidine, morpholine, thiamorpholine, piperazine, and N-methylpiperazine.

OPTICAL ISOMERS—DIASTEREOMERS—GEOMETRIC ISOMERS

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

SALTS

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

UTILITIES

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic aczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) chloecystitis, and 16) tumor metastasis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

DOSE RANGES

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

PHARMACEUTICAL COMPOSITIONS

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (opthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200; and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

COMBINATIONS WITH OTHER DRUGS

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives;
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free $—CH(CH_3)COOH$ or $—CH_2CH_2COOH$ group (which optionally can be in the form of a pharmaceutically acceptable salt group, e.g., $—CH(CH_3)COO^-Na^+$ or $—CH_2CH_2COO^-Na^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free $—CH_2COOH$ group (which optionally can be in the form of a pharmaceutically acceptable salt group, e.g. $—CH_2COO^-Na^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

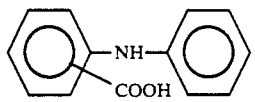

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

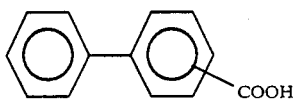

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

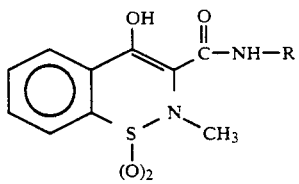

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., Pharmaprojects), may also be used: 480156, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac and tolmetin. Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U. K. Patent Specification No. 2,058,785 (Apr. 15, 1981) which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an H₁- or H₂-receptor antagonist, such as acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a K⁺/H⁺ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

METHODS OF SYNTHESIS

Compounds of the formula I of the present invention may be prepared according to the following method. Temperatures are in degrees Celsius.

SCHEME I

The N-alkylated product III may be prepared by addition of substituted acetate derivative ($XCH_2CO_2R^4$; wherein X=leaving group) such as methyl bromoacetate to the salt of indole II prepared by addition of a base such as sodium hydride to the indole II in an organic solvent such as DMF. The ketone intermediate VII may be prepared by addition of alkyl lithium such as methyl lithium to compound III (wherein $R^4$=H) or alkyl magnesium halide such as isobutyl magnesium chloride to compound III (wherein $R^4$=lower alkyl) in an organic solvent such as diethyl ether. The aldehyde intermediate IV may be prepared by addition of a suitable reducing agent such as diisobutyl aluminum hydride (DiBAL) to compound III in an organic solvent such as toluene. The oxime V is prepared by addition of hydroxylamine hydrochloride to the aldehyde IV or the ketone VII in an alcoholic solvent such as ethanol in the presence of an organic nitrogen base, e.g. pyridine. The oxime V is then converted to the hydroxamino derivative VI by reduction with a suitable reducing agent such as pyridine-borane complex in an acidic alcoholic solvent, e.g. EtOH/HCl. Compounds of the formula I are then obtained from VI by addition of trimethyl-silylisocyanate in an organic solvent such as THF. Subsequent addition of water allows the necessary hydrolysis to the N-hydroxy urea compound I of the invention.

Table I illustrates compounds representative of the present invention.

TABLE 1

Ib

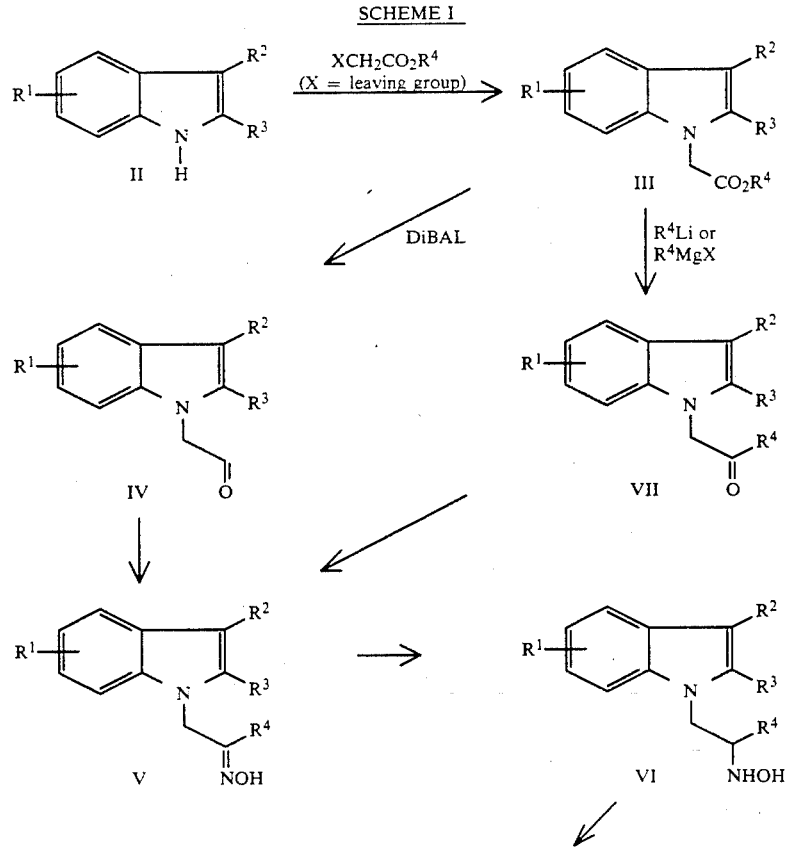

| EX. | $R^1$ | $R^2$ | $R^3$ | $R^4$ |
|---|---|---|---|---|
| 1 | H | $CH_2Ph$ | H | H |
| 2 | H | SPh | H | H |
| 3 | H | SPh | H | Me |
| 4 | H | SPh | H | $CH_2CHMe_2$ |
| 5 | H | SMe | H | Me |
| 6 | H | Cl | H | Me |
| 7 | H | H | H | Me |
| 8 | H | H | SPh | Me |
| 9 | 5-Cl | SPh | H | Me |

SCHEME I

SCHEME I

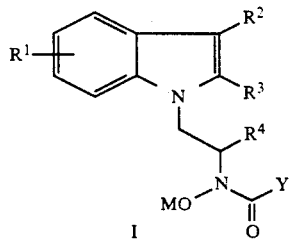

-continued

ASSAYS FOR DETERMINING BIOLOGICAL ACTIVITY

Compounds of Formula I can be tested using the following assays to determine their mammalian leukotriene biosynthesis inhibiting activity.

DETERMINATION OF INHIBITION OF RAT 5-LIPOXYGENASE

The activity of 5-lipoxygenase was measured from the conversion of [$^{14}$C]-arachidonic acid to 5-HETE and 5,12-diHETEs catalyzed by the 10,000×g supernatant fraction from rat PMN leukocytes, using the procedure of Riendeau and Leblanc (*Biochem. Biophys. Res. Commun.*, 141, 534–540, 1986) with minor modifications. The incubation mixture contained 25 mM Na$^+$/K$^+$ phosphate buffer, pH 7.3, 1 mM ATP, 0.5 mM CaCl$_2$, 0.5 mM mercaptoethanol and an aliquot of the enzyme preparation in a final volume of 0.2 ml. The enzyme was pre-incubated with the inhibitor for 2 minutes at 37° C. before initiation of the reaction with the addition of 2 ml of [$^{14}$C]-arachidonic acid (25,000 DPM) in ethanol to obtain a final concentration of 10 mM. Inhibitors were added as 500-fold concentrated solutions in DMSO. After incubation for 10 minutes at 37° C., the reaction was stopped by adding 0.8 mL of diethyl ether/methanol/1M citric acid (30:4:1). The samples were centrifuges at 1,000×g for 5 minutes and the organic phases analyzed by TLC on Baker Si250F-PA or Whatman silica gel 60A LKFG plates using diethyl ether/petroleum ether/acetic acid (50:50:1) as solvent. The amount of radioactivity migrating at the positions of arachiodinic acid, 5-HETE and 5,12-diHETEs was determined using a Berthold TLC analyzer LB 2842. The activity of 5-lipoxygenase was calculated from the percentage of conversion of arachidonic acid to 5-HETE and 5,12-diHETEs after the 10 minute incubation.

RAT PERITONEAL POLYMORPHONUCLEAR (PMN) LEUKOCYTE ASSAY

Rats under ether anesthesia are injected (i.p.) with 8 ml of a suspension of sodium caseinate (6 grams in ca. 50 mL water). After 15–24 hours, the rats are sacrificed (CO$_2$) and the cells from the peritoneal cavity are recovered by lavage with 20 mL of buffer (Eagles MEM containing 30 mM HEPES adjusted to pH 7.4 with NaOH). The cells are pelleted (350×g, 5 minutes), resuspended in buffer with vigorous shaking, filtered through lens paper, recentrifuged and finally suspended in buffer at a concentration of 10 cells/mL. A 500 mL aliquot of PMN suspension and test compound are preincubated for 2 minutes at 37°, followed by the addition of 10 mM A-23187. The suspension is stirred for an additional 4 minutes then bioassayed for LTB$_4$ content by adding an aliquot to a second 500 mL portion of the PMN at 37° C. The LTB$_4$ produced in the first incubation causes aggregation of the second PMN, which is measured as a change in light transmission. The size of the assay aliquot is chosen to give a submaximal transmission change (usually −70%) for the untreated control. The percentage inhibition of LTB$_4$ formation is calculated from the ratio of transmission change in the sample to the transmission change in the compound-free control.

HUMAN POLYMORPHONUCLEAR (PMN) LEUKOCYTE LTB$_4$ ASSAY

A. Preparation of Human PMN. Human blood is obtained by anticubital venepuncture from consenting volunteers who have not taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation of erythrocytes followed by centrifugation through Ficoll-Hypaque (specific gravity 1.077), as described by Boyum, A., *Scand. J. Clin. Lab. Invest.*, 1968, 21 (Supp 97), 77. Contaminating erythrocytes are removed by lysis following exposure to ammonium chloride (0.16M) in Tris buffer (pH 7.65), and PMNs resuspended at 5×10$^5$ cells/mL in HEPES (15 mM)-buffered Hanks balanced salt solution containing Ca$^{2+}$ (1.4 mM) and Mg$^{2+}$ (0.7 mM), pH 7.4. Viability is assessed by Trypan blue exclusion.

B. Generation and Radioimmunoassay of LTB$_4$. PMNs (0.5 mL; 2.5×10$^5$ cells) are placed in plastic tubes and incubated (37° C., 2 minutes) with test compounds at the desired concentration or vehicle (DMSO, final concentration 0.2%) as control. The synthesis of LTB$_4$ is initiated by the addition of calcium ionophore A23187 (final concentration 10 mM) or vehicle in control samples and allowed to proceed for 5 minutes at 37° C. The reactions are then terminated by the addition of cold methanol (0.25 mL) and samples of the entire PMN reaction mixture removed for radioimmunoassay of LTB$_4$.

Samples (50 mL) of authentic LTB$_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes. Thereafter, [$^3$H]-LTB$_4$ (10 nCi in 100 mL RIA buffer) and LTB$_4$-antiserum (100 mL of a 1:3000 dilution in RIA buffer) are added and the tubes vortexed. Reactants are allowed to equilibrate by incubation overnight at 4° C. To separate antibody-bound from free LTB$_4$, aliquots (50 mL) of activated charcoal (3% activated charcoal in RIA buffer containing 0.25% Dextran T-70) are added, the tubes vortexed, and allowed to stand at room temperature for 10 minutes prior to centrifugation (1500×g; 10 minutes; 4° C.). The supernatants containing antibody-bound $LTB_4$ are decanted into vials and Aquasol 2 (4 mL) added. Radioactivity is quantified by liquid scintillation spectrometry. The specificity of the antiserum and the sensitivity of the procedure have been described by Rokach et al., *Prostaglandins Leukotrienes and Medicine*, 1984, 13, 21. The amount of $LTB_4$ produced in test and control samples is calculated. Inhibitory dose-response curves are constructed using a four-parameter algorithm and from these the $IC_{50}$ values determined.

ASTHMATIC RAT ASSAY

Rats are obtained from an inbred line of asthmatic rats. Both femal (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mgm/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

PULMONARY MECHANICS IN TRAINED CONSCIOUS SQUIRREL MONKEYS

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65 HG, 400 cps) and given in a volume of 1 ml/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or Ascaris antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., *Prostaglandins*, 28:173-182, 1984, and McFarlane, C. S. et al., *Agents Actions* 22:63-68, 1987.)

PREVENTION OF INDUCED BRONCHOCONSTRICTION IN ALLERGIC SHEEP

A. Rationale

Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods

Animal Preparation

Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.) and b) they have previously responded to inhalation challenge with *Ascaris suum* with both an acute bronchoconstriction and a late bronchial obstruction (Abraham, W. M. Delehunt, J. C., Yerger, L. and Merchette, B., *Am. Rev. Resp. Dis.*, 1983, 128, 839-44).

Measurement of Airway Mechanics

The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems

Aerosols of *Ascaris suum* extract (1:20) are generated using a disposable medicalnebulizer (Raindrop ®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from nebulizer is directed into a plastic t-piece, one end of which is attached to the nasotracheal tube, the other end of which is conected to the inspiratory part of a Harvard respirator. The aerosol is delivered at a tidal volume of 500 ml of a rate of 20 per minute. Thus, each sheep receives an equivalent dose of antigen in both placebo and drug trials.

Experimental Protocol

Prior to antigen challenge baseline measurements of $SR_L$ are obtained, infusion of the test compound is started 1 hr. prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs. after antigen challenge. Placebo and drug tests are separated by at least 14 days. In a further study, sheep are given a bolus dose of the test compound followed by an infusion of the test compound for 0.5-1 hr. prior to Ascaris challenge and for 8 hrs. after Ascaris as described above.

Statistical Analysis

A Kruskal-Wallis one way ANOVA test is used to compare the acute immediate responses to antigen and the peak late response in the controls and the drug treated animals.

The invention is further defined by reference to the following examples, which are intended to be illustrative and not limiting. All temperatures are in degrees Celsius.

EXAMPLE 1

N-[2-(3-Benzylindol-1-yl)eth-1-yl]-N-hydroxy urea

Step 1: Methyl (3-benzylindol-1-yl)acetate

To a suspension of NaH (50% dispersion in oil, 170 mg, 3.5 mmol) in DMF (15 mL), at r.t. and under an atmosphere of nitrogen, there was added in portions 3-benzylindole (ref: Tetrahedron 23, 3771-83 (1967)) (621 mg, 3 mmol) and the mixture was stirred for 1 hour. There added methyl bromoacetate (765 mg, 5 mmol) and stirring was continued for 1.5 hours. $H_2O$ (100 mL) was added and the mixture was extracted twice with $Et_2O$. These extracts were $H_2O$ with water, dried over $MgSO_4$ and evaporated to a residue which was chromatographed on silica gel eluting with a 1:5 mixture of EtOAc acetate and hexane to afford the title product as an oil.

Step 2: (3-Benzylindol-1-yl)acetaldehyde

To a solution of the product from Step 1 (470 mg, 1.68 mmol) in toluene (15 mL) at −65° C. there was slowly added 1.0M DIBAL in toluene (2.24 mL, 2.24 mmol) and the mixture was stirred at −65° C. for 1 hour. There was slowly added MeOH (5 mL) and the mixture was then allowed to warm up to r.t. There was added $H_2O$ (20 mL) and 1N aqueous HCl (10 mL) and after shaking the organic phase was washed with $H_2O$, dried over $MgSO_4$ and evaporated down to an oily residue which was taken as such to the next step.

Step 3: 3-Benzyl-1-(2-hydroximinoethyl)indole

To a solution of the aldehyde from Step 2 (390 mg, 1.57 mmol) in EtOH (6 mL) there was added hydroxylamine hydrochloride (435 mg, 6.26 mmol), then pyridine (3 mL). The mixture was stirred at r.t. for 45 minutes, then it was evaporated to dryness. The residue was partitioned between $Et_2O$ and $H_2O$, and by evaporation of the ethereal fraction the title oxime was obtained as a soft solid.

Step 4: 3-Benzyl-1-(2-hydroxaminoethyl)indole

To a solution of the oxime from Step 3 (400 mg, 1.52 mmole) in EtOH (7 mL) at 0° C. there was added pyridine-borane complex (288.5 mg, 3.10 mmole) and 4M ethanolic HCl (1.16 mL, 4.65 mmol). The mixture was stirred at 0° C. for 20 minutes, then allowed to warm up to r.t. Most of the EtOH was evaporated away, $H_2O$ (20 mL) and 1N aqueous HCl (10 mL) was added, and the mixture was extracted twice with $Et_2O$. The aqueous fraction was then made basic with 2.5N aqueous NaOH, and extracted twice with $Et_2O$. From these extracts a crude product was obtained which was purified by chromatography on silica gel, eluting with 5% EtOH in $CH_2Cl_2$ to afford the title product as a colorless oil.

Step 5: N-[2-(3-Benzylindol-1-yl)eth-1-yl]-N-hydroxy urea

To a solution of product from Step 4 (150 mg, 0.56 mmol) in THF (4 mL) at room temperature there was added 85% trimethyl silyl isocyanate (TMSNCO, 162 mg, 1.2 mmol) and the mixture was stirred for 30 minutes. $H_2O$ (5 mL) was added, and after stirring for a further 10 minutes the THF was evaporated, and the residue extracted with $Et_2O$, the extracts washed with $H_2O$, dried over $MgSO_4$ and evaporated to afford the title compound as a thick oil.

¹H NMR, 250 mHz (CDCl₃) δ3.80 (t, J=6.2 Hz, CH₂), 4.07 (s, CH₂), 4.24 (t, J=6.2 Hz, CH₂), 4.98 (br-s, NH₂), 6.80 (br-s, OH), 6.83 (s, H-2), 7.06 (t, J=7.8 Hz, H-5 or H-6), 7.16-7.27 (m, 6H, arom), 7.34 (d, J=8.0 Hz, H-7), 7.51 (d, J=7.6 Hz, H₄).

EXAMPLE 2

N-[2-(3-Phenylthioindol-1-yl)eth-1-yl]-N-hydroxy urea

Following the procedures described in Example 1, Steps 1-5, but substituting 3-phenyl thioindole (J. Het. Chem. 1979, 16, 567) for 3-benzylindole as starting material, the title compound was obtained as a thick oil which slowly solidified, m.p.: 95°-99° C.

EXAMPLE 3

N-[1-(3-Phenylthioindol-1-yl)prop-2-yl]-N-hydroxy urea

Step 1: 1-(2-Oxopropyl)indole

To a solution of indole-N-acetic acid (KNK, 10 g, 57 mmol) in dry ether (150 mL) was added dropwise at 0° C. a solution of MeLi (75 mL, 1.4M in ether as LiBr complex). The reaction mixture was then stirred at r.t. for 2 hrs. Chlorotrimethylsilane (70 mL, 0.57 mol) was added dropwise at 0° C. Then the cooling bath was removed and 1N HCl (70 mL) was added at r.t. The aqueous portion was extracted with ethyl acetate and the combined organic phase was washed with brine, dried over MgSO₄ and evaporated. Purification by flash chromatography using 30% ethyl acetate in hexanes gave the title compound.

Step 2: 1-(2-Oxopropyl)-3-phenylthioindole

To a solution of diphenyl disulfide (378 mg, 1.73 mmol) in 1,2-dichloroethane (10 mL) there was added at room temperature sulfuryl chloride (233 mg, 1.73 mmol) and the resulting yellow solution was stirred at r.t. for 15 minutes. This solution was slowly added to a cooled (0° C.) solution of ketone from Step 1 (500 mg, 2.89 mmol) in CH₂Cl₂ (10 mL). The mixture was stirred at 0° C. for 30 minutes, then poured onto saturated aqueous NaHCO₃ solution, and extracted with CH₂Cl₂. The organic phase was washed with brine, dried and evaporated to a residue which was chromatographed on silica gel, eluting with EtOAc (1:3) to afford the title product.

Step 3: N-[1-(3-Phenylthioindol-1-yl)prop-2-yl]-N-hydroxy urea

Following the procedures described in Example 1, Steps 3 to 5, but substituting the product from Step 2 for (3-benzylindole-1-yl)acetaldehyde as starting material, the title compound was obtained as a solid, m.p.: 73°-76° C.

EXAMPLE 4

N-[4-Methyl-1-(3-phenylthioindol-1-yl)pent-2-yl]-N-hydroxy urea

Step 1: 1-(4-Methyl-2-oxopentyl)indole

To a solution of methyl indol-1-ylacetate (1.13 g, 5.9 mmol) from Example 1, Step 1, in THF at −78° C. was added dropwise a solution of 2M isobutyl magnesium chloride in Et₂O (3.3 mL, 6.6 mmol). The reaction mixture was warmed up to 0° C. and kept at this temperature until the starting material disappeared. The reaction mixture was quenched with a 0.5M solution of Na and K tartrate and extracted with EtOAc. The extract was washed with a solution of NH₄OAc, dried over MgSO₄ and evaporated to dryness. The crude residue was chromatographed on flash silica gel column eluting with EtOAc-hexane (1:9) to afford the pure title product.

Step 2: 3-Phenylthio-1-(4-methyl-2-oxopentyl)indole

Following the procedure described in Example 3, Step 2, but substituting the ketone from Step 1 for 1-(2-oxopropyl)indole as starting material the title product was obtained.

Step 3: N-[4-Methyl-1-(3-phenylthioindol-1-yl)pent-2-yl]-N-hydroxy urea

Following the procedures described in Example 1, Steps 3 to 5, but substituting the ketone from Step 2 for (3-butylindol-1-yl)acetaldehyde as starting material the title compound was obtained, m.p.: 57° C.

EXAMPLE 5

N-[1-(3-Methylthioindol-1-yl)prop-2-yl]-N-hydroxy urea

Step 1: 1-(2-Oxopropyl)-3-methylthioindole

Following the procedure described in Example 3, Step 2, but substituting dimethyl disulfide for diphenyl disulfide as starting material, the title product was obtained.

Step 2: N-[1-(3-Methylthioindol-1-yl)prop-2-yl]-N-hydroxy urea

Following the procedures described in Example 1, Steps 3 to 5, but substituting the ketone from Step 1 for (3-benzylindol-1-yl)acetaldehyde, the title compound was obtained as a solid, m.p.: 87°-90° C.

EXAMPLE 6

N-[1-(3-Chloroindol-1-yl)prop-2-yl]-N-hydroxy urea

Step 1: 3-Chloro-1-(2-oxopropyl)indole

To a solution of 1-(2-oxopropyl)indole from Example 3, Step 1 (800 mg, 4.6 mmol) in dry THF (20 mL) was added in one portion at r.t. N-chlorosuccinimide (680 mg, 5.1 mmol). The resulting reaction mixture was stirred at room temperature for 1.5 hours. Ethyl acetate was then added (200 mL) and the organic phase was washed successively with 1N HCl, saturated NaHCO₃, brine, dried and evaporated. The crude product was purified by flash chromatography eluting with 25% EtOAc in hexanes to yield the title compound.

Step 2: N-[1-(3-Chloroindol-1-yl)prop-2-yl]-N-hydroxy urea

Following the procedures described in Example 1, Steps 3 to 5, but substituting the product from Step 1 for (3-benzylindol-1-yl)acetaldehyde as starting material, the title compound was obtained as a solid, m.p.: 168°-171° C.

EXAMPLES 7 AND 8

N-[2-(Indol-1-yl)eth-1-yl]-N-hydroxy urea and N-[2-(2-Phenylthioindol-1-yl)eth-1-yl]-N-hydroxy urea A mixture of N-[1-(3-phenylthioindol-1-yl)prop-2-yl]-N-hydroxy urea from Example 3 (100 mg, 0.34 mmol), thiosalicylic acid (208 mg, 1.4 mmol) and trifluoroacetic acid (3 mL) was stirred at r.t. for one hour. The reaction mixture was then poured onto an aqueous saturated NaHCO$_3$ solution and extracted with EtOAc. The combined organic phase was then washed with 1N NaOH, brine, dried and evaporated to dryness. Separation of two products by flash chromatography using 90% EtOAc in hexanes gave the N-[2-(indol-1-yl)eth-1-yl]-N-hydroxy urea, m.p.: 150°–152° C., and the N-[2-(2-phenylthioindole-1-yl)eth-1-yl]-N-hydroxy urea, m.p.: 57°–60° C.

EXAMPLE 9

N-[1-(5-Chloro-3-phenylthioindol-1-yl)prop-2-yl]-N-hydroxy urea

Step 1: (5-Chloroindol-1-yl)acetic acid

To a suspension of NaH 60% dispersion in oil (1.52 g, 38 mmol) in DMF (50 mL) at r.t. there was added, in portions, 5-chloroindole (5.0 g, 33 mol) and the mixture was stirred for 30 minutes. There was added ethyl bromoacetate (7.44 g, 44 mmol) and the mixture was stirred for a further 5 hours. H$_2$O (200 mL) was added and the mixture was extracted with Et$_2$O. These extracts were washed with H$_2$O, dried over MgSO$_4$ and evaporated to a crude oily residue. Chromatography on silica gel, eluting with 5% EtOAc in toluene, afforded the ethyl ester of the title compound contaminated with some 5-chloroindole. This mixture was dissolved in EtOH (100 mL) and 2.5N aqueous NaOH was added (50 mL). The mixture was stirred at r.t. for 2 hours, then concentrated to a small volume. This residue was partitioned between H$_2$O and Et$_2$O, and by acidification of the aqueous fraction with 6N aqueous HCl, the title compound precipitated. The precipitate was filtered, washed with H$_2$O and air-dried to afford the pure title product as a cream-colored solid.

Step 2: 5-Chloro-1-(2-oxopropyl)indole

To a solution of acid from Step 1 (1.048 g, 5 mmol) in CH$_2$Cl$_2$ (45 mL) at r.t. there was added oxalyl chloride (762 mg, 6 mmol) and 2 drops of DMF. The mixture was stirred at r.t. for 1 hour, then it was added slowly to a cooled (0° C.) solution of 2,2-dimethyl-1,3-dioxan-4,6-dione (864 mg, 6 mmol) in CH$_2$Cl$_2$ (10 mL) and pyridine (1 mL). The resulting mixture was stirred at 0° C. for 30 minutes, then at r.t. for 1.5 hours. The CH$_2$Cl$_2$ was evaporated, there was added a mixture of HOAc (15 mL) and H$_2$O (30 mL), and the mixture was heated at 90° C. for 45 minutes. After dilution with H$_2$O, the mixture was extracted twice with EtOAc, and these combined extracts were washed with H$_2$O, dried and evaporated to a residue which was chromatographed on silica gel, eluting with EtOAc-hexane (1:2) to afford the title compound as a yellow oil.

Step 3: N-[1-(5-Chloro-3-phenylthioindol-1-yl)prop-2-yl]-N-hydroxy urea

Following the procedures described in Example 1, Steps 3–5, but substituting the product from Step 1 (3-benzylindol-1-yl)acetaldehyde as starting material, the title compound was obtained as a white solid, m.p.: 181° C. (dec).

What is claimed is:
1. A compound of the formula:

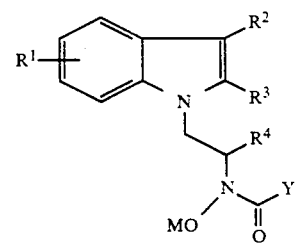

wherein:
R$^1$, R$^2$ and R$^3$ are independently:
a) hydrogen;
b) lower alkyl;
c) cycloalkyl;
d) CH$_2$(phenyl-R$^8$);
f) NO$_2$;
g) CF$_3$;
h) N$_3$;
i) N(R$^5$)$_2$, NR$^4$COR$^6$, or NR$^4$CON(R$^5$)$_2$, wherein R$^5$ is not H;
k) SR$^7$, S(O)R$^7$, S(O)$_2$R$^7$, or S(O)$_2$N(R$^5$)$_2$, wherein R$^5$ is not H;
l) COR$^6$, CON(R$^5$)$_2$, CO$_2$R$^4$, wherein R$^5$ is not H; or
m) halogen;
R$^4$ H or lower alkyl;
R$^5$ is H or loweralkyl.
R$^6$ is H, loweralkyl, -phenyl-R$^8$, or CF$_3$;
R$^7$ is lower alkyl, phenyl-R$^8$, or CF$_3$;
R$^8$ is:
a) H;
b) lower alkyl;
c) lower alkylthio;
d) CN;
e) CF$_3$;
f) N$_3$;
g) NR$^4$COR$^4$;
h) OR$^4$;
i) COR$^4$, CON(R$^5$)$_2$, or CO$_2$R$^4$; or
j) halogen;
Y is H, lower alkyl, or N(R$^5$)$_2$;
M is H, CO(phenyl-R$^8$), or CO-alkyl;
cycloalkyl is cyclopropyl, cyclopentyl, cycloheptyl, adamantyl, cyclododecylmethyl, or 2-ethyl-1-bicyclo[4.4.0]decyl;
lower alkyl is C$_1$–C$_7$ lower alkyl;
or the pharmaceutical acceptable salts thereof.

2. A compound of claim 1 of formula Ib:

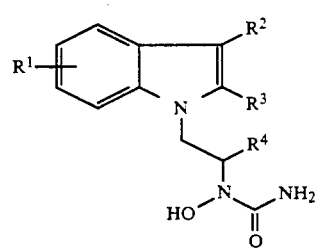

wherein the substituents are follows:

| EX. | R$^1$ | R$^2$ | R$^3$ | R$^4$ |
|---|---|---|---|---|
| 1 | H | CH$_2$Ph | H | H |
| 2 | H | SPh | H | H |
| 3 | H | SPh | H | Me |

-continued

| EX. | R¹ | R² | R³ | R⁴ |
|-----|------|-----|-----|------------|
| 4 | H | SPh | H | $CH_2CHMe_2$ |
| 5 | H | SMe | H | Me |
| 6 | H | Cl | H | Me |
| 7 | H | H | H | Me |
| 8 | H | H | SPh | Me |
| 9 | 5-Cl | SPh | H | Me |

3. A pharmaceutical composition comprising a therapeutically effective amount of a compound of claim 1 and a pharmaceutically acceptable carrier.

4. A method of preventing the synthesis, the action, or the release of SRS-A or leukotrienes in a mammal which comprises administering to said mammal an effective amount of a compound of claim 1.

5. The method of claim 4 wherein the mammal is man.

6. A method of treating asthma in a mammal comprising administering to a mammal in need of such treatment a therapeutically effective amount of a compound of claim 1.

7. A method of treating inflammatory diseases of the eye in a mammal which comprises administering to a mammal in need of such treatment a therapeutically effective amount of a compound of claim 1.

8. The method of claim 7 wherein the mammal is man.

* * * * *